US00PP10942P

United States Patent [19]

Bergman

[11] Patent Number: Plant 10,942

[45] Date of Patent: Jun. 8, 1999

[54] HIBISCUS PLANT NAMED 'VELVET WIND'

[75] Inventor: Wendy R. Bergman, Lehigh Acres, Fla.

[73] Assignee: Yoder Brothers, Inc., Barberton, Ohio

[21] Appl. No.: 08/995,358

[22] Filed: Dec. 22, 1997

[51] Int. Cl.[6] ..... A01H 5/00

[52] U.S. Cl. ..... Plt./257

[58] Field of Search ..... Plt./67.8, 257

[56] References Cited

PUBLICATIONS

Usher. The Wordworth Dictionary of Botany. p. 274, 1966.

*Primary Examiner*—Elizabeth Kemmerer
*Assistant Examiner*—Melissa L. Kimball
*Attorney, Agent, or Firm*—C. A. Whealy

[57] ABSTRACT

A new and distinct cultivar of Hibiscus plant name 'Velvet Wind', characterized by its shiny and very dark green leaves; upright, uniform, dense and symmetrical plant habit that is appropriate for container production; floriferousness with numerous red-colored flowers with dark red to purple throats; good resistance to flower bud abscission; and excellent postproduction longevity.

1 Drawing Sheet

The present invention relates to a new and distinct cultivar of Hibiscus, botanically known as *Hibiscus rosa-sinensis,* and hereinafter referred to by the cultivar name 'Velvet Wind'.

The new cultivar is a product of a planned breeding program conducted by the inventor of Alva, Fla. The objective of the breeding program is to create new Hibiscus cultivars having uniform and compact plant habits appropriate for container production, early and uniform flowering, numerous flower per lateral branch, desirable flower color, resistance to flower bud abscission, and good postproduction longevity.

The new cultivar originated from a cross made by the inventor in Alva, Fla., of a proprietary *Hibiscus rosa-sinensis* selection, designated as code No. 675, as the female, or seed, parent with the *Hibiscus rosa-sinensis* cultivar Waikiki (disclosed in U.S. Plant Pat. No. 7,834) as the male, or pollen, parent. The cultivar 'Velvet Wind' was discovered and selected by the inventor as a flowering plant within the progeny of the stated cross in a controlled environment in Alva, Fla., on Sep. 24, 1993.

Compared to plants of the female parent, the proprietary Hibiscus selection code No. 675, plants of the new Hibiscus have better budding uniformity, flower much earlier, and are more floriferous. Plants of new Hibiscus differ from plants of the male parent, the cultivar Waikiki, in flower color. In addition, plants of the new Hibiscus are more compact, have slightly smaller but more flowers, and have leaves that are darker and glossier than plants of the male parent, the cultivar Waikiki.

Asexual reproduction of the new cultivar by terminal cuttings taken in a controlled environment in Alva, Fla., has shown that the unique features of this new Hibiscus are stable and reproduced true to type in successive generations.

The cultivar 'Velvet Wind' has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Velvet Wind'. These characteristics in combination distinguish 'Velvet Wind' as a new and distinct cultivar:

1. Shiny and very dark green leaves.
2. Upright, uniform, dense and symmetrical plant habit that is appropriate for container production.
3. Very freely flowering, numerous red-colored flowers with darker red to purple throats.

4. Good resistance to flower bud abscission.
5. Excellent postproduction longevity.

Plants of the new Hibiscus can be compared to plants of the nonpatented cultivar Crimson Tide. However, in side-by-side comparisons conducted in Alva, Fla., plants of the new cultivar differ from plants of the cultivar Crimson Tide in the following characteristics:

1. Plants of the new Hibiscus are more upright than plants of the cultivar Crimson Tide.
2. Plants of the new Hibiscus have darker green and glossier leaves than plants of the cultivar Crimson Tide.
3. Flowers of plants of the new Hibiscus are brighter red in color than flowers of plants of the cultivar Crimson Tide.
4. Plants of the new Hibiscus flower about 10 days later than plants of the cultivar Crimson Tide.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of typical plant of 'Velvet Wind'.

The photograph at the bottom of the sheet comprises a close-up view of a typical flower of 'Velvet Wind'. Flower and foliage colors in the photographs may appear different from the actual colors due to light reflectance.

DETAILED BOTANICAL DESCRIPTION

The following observations, measurements and values describe plants grown in Alva, Fla., and Keller, Tex., in 28-cm containers during the summer and early autumn with day temperatures ranging from 16 to 35° C. and night temperatures ranging from 10 to 24° C. In the description, color referencs are made to The Royal Horticultural Society Colour Chart except where general terms of ordinary dictionary significance are used.

Botanical classification: *Hibiscus rosa-sinensis* cultivar 'Velvet Wind'.

Parentage:

*Female or seed parent.*—*Hibiscus rosa-sinensis* proprietary selection designated as code No. 675.

*Male or pollen parent.*—*Hibiscus rosa-sinensis* cultivar Waikiki, disclosed in U.S. Plant Pat. No. 7,834.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorus, thick and well-branched.

Plant description:

*Plant form and growth habit.*—Perennial, evergreen, upright uniform, dense and symmetrical plant habit. Moderate vigor.

*Branching habit.*—Freely branching, usually five to six lateral branches develop after removal of terminal apex.

*Plant height, soil level to top of flowers.*—About 46 cm.

*Plant diameter, area of spread.*—About 35 cm.

*Lateral branch description.*—Length: About 40 cm. Diameter: About 1 cm. Texture: Immature, smooth; woody with age.

*Color.*—Immature: 166A. Mature: Brown.

Foliage description:

*Arrangement.*—Alternate, single.

*Length.*—About 7.5 cm.

*Width.*—About 6 cm.

*Shape.*—Ovate.

*Apex.*—Acuminate.

*Base.*—Obtuse.

*Margin.*—Serrated.

*Texture.*—Glabrous and very shiny on both surfaces.

*Color.*—Young foliage, upper surface: Darker and greener than 146A. Young foliage, lower surface: 146A. Mature foliage, upper surface: Very dark green, much darker than 147A. Mature foliage, lower surface; 147A; veins, 166A.

*Petiole.*—Length: About 3.25 cm. Diameter: About 2.5 mm. Texture: Smooth or with very fine pubescence on upper surface. Color: Close to 166A.

Flower description:

*Natural flowering season.*—Usually spring and summer or during periods of warm weather.

*Flower arrangement.*—Flowers arranged singly at terminal leaf axils. Very freely flowering with usually five to seven flower buds and/or open flowers per terminal apex. Flowers flat and face upright.

*Flower appearance.*—Star-shaped single. Red-colored petals with darker red to purple throat. Flowers are open for about one day before closing. Flowers self-cleaning.

*Flower diameter.*—About 11 cm.

*Flower bud* (*just before showing color*).—Rate of opening: About one day depending on temperatures. Length: About 2 cm. Diameter: About 1 cm. Shape: Columnar, oblong.

*Petals.*—Texture: Crepe, slightly ruffled. Arrangement: Corolla consists of five petals that overlap. Shape: Spatulate with rounded apex. Margin: Entire, but slightly ruffled. Length: About 7 cm. Width: About 5 cm. Color: Opening: 45A. Upper surface: 45B/45C. Lower surface: 45A/45B. Yellowish, 11C, at right edges of petal. Throat: Dark red to purple, 53A to 59A.

*Sepals.*—Appearance: Six sepals fused into a star-shaped calyx. Shape: Linear. Texture: Smooth. Color, outer surface: 146A.

*Peduncles.*—Length: About 4.25 cm. Diameter: About 3 mm at apex. Angle: Very upright. Strength: Very strong and rigid. Color: Close to 166A with green overtones.

*Reproductive organs.*—Androecium: Stamen number: Numerous. Stamen length: About 5 mm. Anther size: About 1 mm. Amount of pollen: Abundant. Pollen color: 21A. Gynoecium: Pistil length: About 8.5 cm. Style color: Apex: 51A. Base: 59A/46A to 47A. Stigma number: Five. Stigma shape: Round. Stigma diameter: About 2 mm. Stigma color: Slightly darker than 46A. Ovary color: Light green, 154C with small reddish speckles.

Disease resistance: No known Hibiscus diseases observed to dat on plants grown under commercial greenhouse conditions.

Seed production: If cross-pollinated, seed production may be observed. Usually one to twenty seeds per capsule.

It is claimed:

1. A new and distict Hibiscus plant named 'Velvet Wind', as illustrated and described.

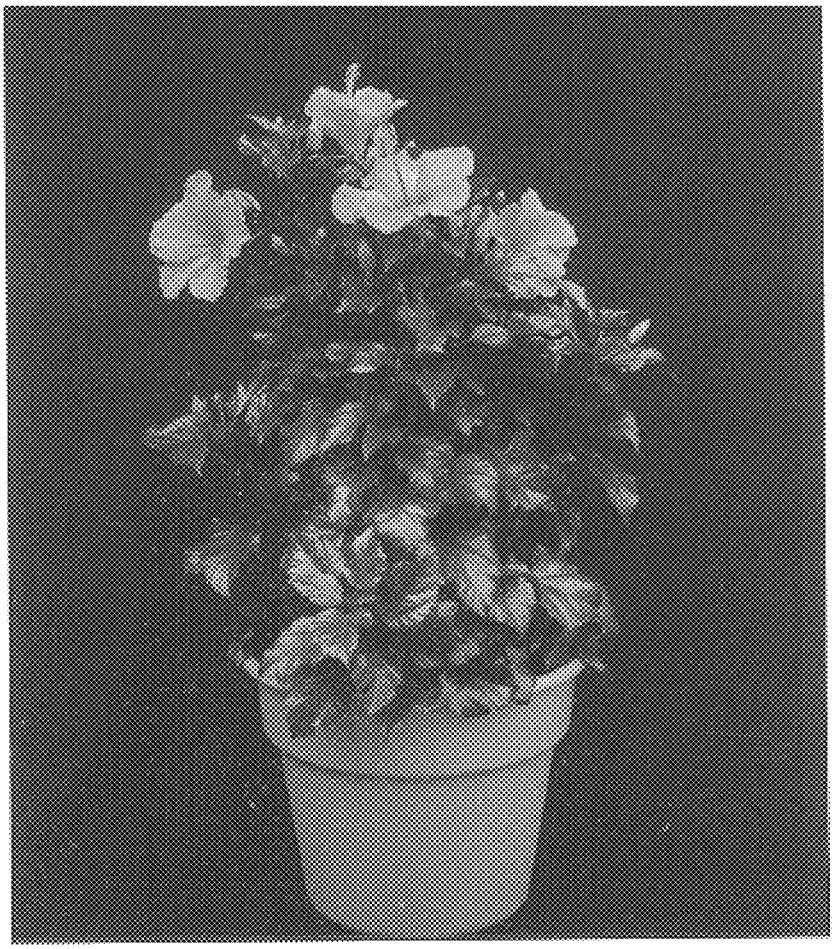
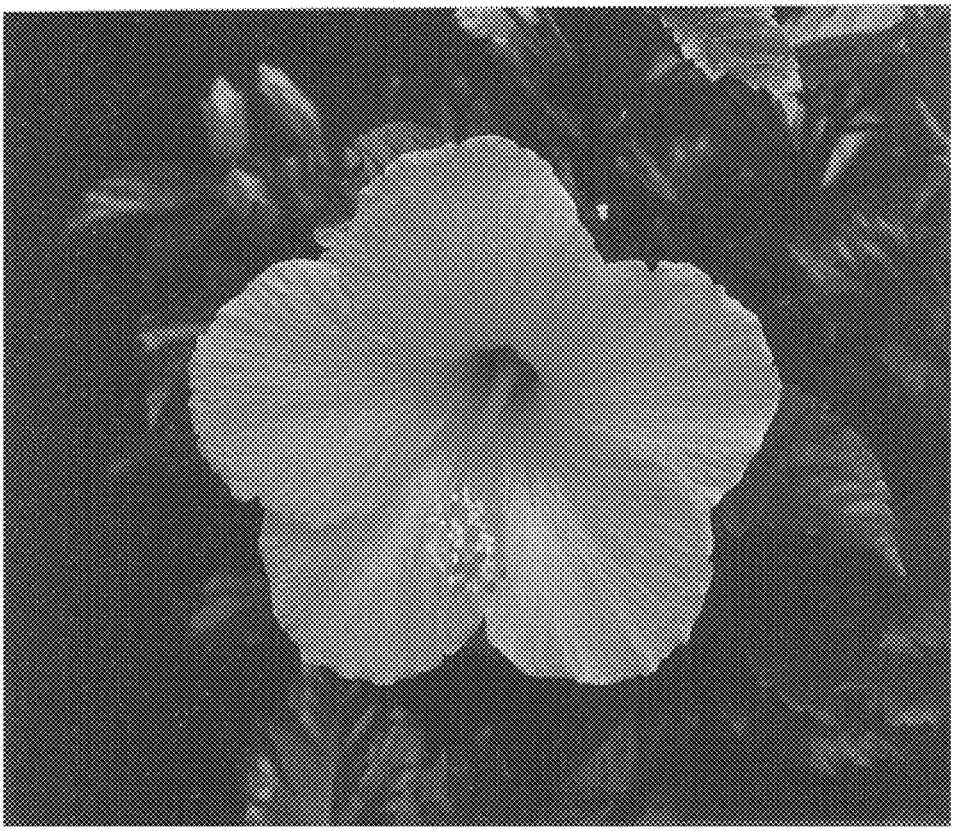

* * * * *